United States Patent [19]

Ecke, Jr.

[11] Plant 4,809

[45] Jan. 19, 1982

[54] POINSETTIA NAMED V-10 WHITE

[75] Inventor: Paul Ecke, Jr., Encinitas, Calif.

[73] Assignee: Paul Ecke Ranch, Encinitas, Calif.

[21] Appl. No.: 185,124

[22] Filed: Sep. 5, 1980

[51] Int. Cl.[3] ..... A01H 5/00

[52] U.S. Cl. ..... Plt./86

[58] Field of Search ..... Plt./86

*Primary Examiner*—Robert E. Bagwill

*Attorney, Agent, or Firm*—Rummler and Snow

[57] ABSTRACT

A new variety of poinsettia plant distinguished by having the unique characteristics of the red GUTBIER'S V-10 (U.S. Plant Pat. No. 4,235) in all respects except that the new plant has a distinct white color.

1 Drawing Figure

BACKGROUND OF THE NEW PLANT

This new poinsettia variety originated as a mutation of its parent, GUTBIER'S V-10 PINK (Ser. No. 185,123), which, in turn, was a mutation of the red variety, GUTBIER'S V-10 (U.S. Plant Pat. No. 4,235), this new plant resulting from many trials and attempts carried on by me at Encinitas, Calif., with the object of obtaining a good white variety having the advantageous characteristics of the said GUTBIER'S V-10. Upon my selection of this unique white mutation, I propagated the plant, by cuttings, through successive generations and found that its distinctive characteristics held true from generation to generation and appear to be firmly fixed.

DESCRIPTION OF THE DRAWINGS

This new poinsettia cultivar is illustrated by the accompanying full color photographic drawings, of which the upper one is a full face view of the mature bloom and the lower view shows a potted plant in full bloom to illustrate its spreading characteristic.

DESCRIPTION OF THE NEW PLANT

The following is a detailed description of my new poinsettia plant variety as observed at Encinitas, Calif., with color designations according to the R.H.S. Colour Chart published by The Royal Horticultural Society of London, England.

THE PLANT

Origin: Mutation.

Parentage: GUTBIER'S V-10 PINK (application Ser. No. 185,123).

Classification:

*Botanic.—euphorbia pulcherrima.*

*Commercial.—Greenhouse chrysanthemum*

Form: Shrub.

Height: Short.

Growth habit:

*As a single stem.*—Upright and vigorous with self branching side shoots; usually will not require growth regulator.

*As a branched plant.*—Upright with many stems producing a bushy, full appearance.

Growth rate: Very fast, rooting occurring in about 10 to 15 days under automatic mist with the plant blooming in 8 to 9 weeks at night temperatures of 14° to 16° C.

Foilage: Alternate, horizontal, and normal abundance.

*Leaf size.*—Medium; 3 to 6 inches long and about 2½ to 4½ inches wide.

*Leaf shape.*—Ovate, with acuminate apex and substantially entire margins.

*Aspect.*—Upper side—smooth and medium glossy. Under side—dull with ordinary veining.

*Color.*—Upper side—dark green, RHS 139A. Under side—dark green, RHS 137A.

*Retention.*—The foliage lasts well when kept at a low room temperature, that is below 20° C., and with good light intensity.

Bracts: Usually about 12 to 16 in number in generally imbricate arrangement with a tight center which provides a full effect. Mature and over-ripe blooms develop increasing numbers of bracts, often as many as 25 to 30, which cascade in two or three layers thereby increasing the fullness of the bloom. Many of the bracts have a unique arched appearance.

*Size.*—Various, up to about 6 inches long and 4 inches wide.

*Shape.*—Ovate, acuminate apex and substantially entire margin. Small bracts are elliptic.

*Color.*—Upper side and under side—white, near RHS 160C.

Ribs and veins.—Light green in color appearing on the under side of the bracts.

In general, this new white poinsettia plant is the same in substantially all respects, except color, as the red variety GUTBIER'S V-10 and is thus a very attractive and valuable addition to the poinsettia market.

I claim:

1. The new and distinctive poinsettia cultivar, substantially as herein shown and described, characterized by the white coloration of its tight mass of bracts appearing over an abundant display of dark green foilage and by its retention of the important distinguishing characteristics of its grandparent GUTBIER'S V-10.

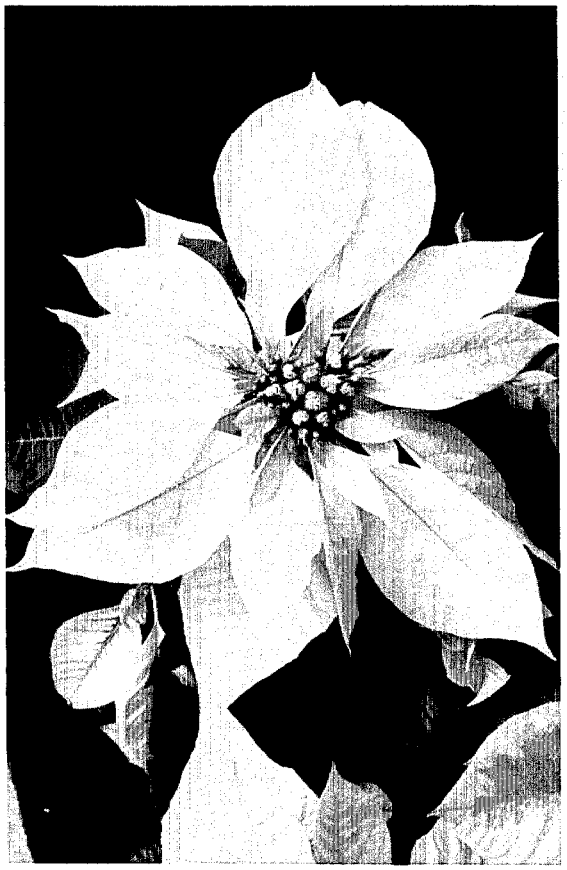
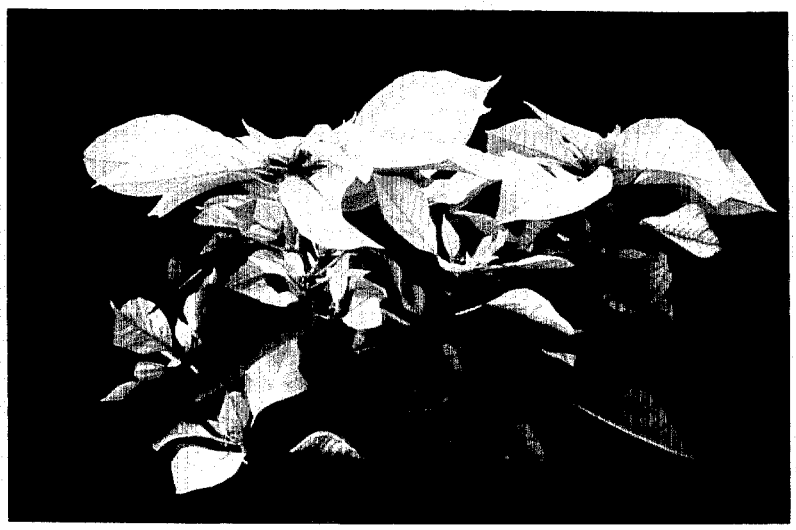

* * * * *